United States Patent [19]
Hofer et al.

[11] 4,107,301
[45] Aug. 15, 1978

[54] O,O'-DIALKYL-O,O'-[2-AMINOPYRIMIDIN(4,6)DIYL]-BIS-[(THIONO)(THIOL)PHOSPHORIC(PHOSPHONIC) ACID ESTERS]

[75] Inventors: Wolfgang Hofer; Fritz Maurer; Hans-Jochem Riebel, all of Wuppertal; Ingeborg Hammann, Cologne; Wolfgang Behrenz, Overath, all of Germany

[73] Assignee: Bayer Aktiengesellschaft, Leverkusen, Germany

[21] Appl. No.: 790,351

[22] Filed: Apr. 25, 1977

[30] Foreign Application Priority Data

May 6, 1976 [DE] Fed. Rep. of Germany ....... 2620089

[51] Int. Cl.² .................. A61K 31/665; C07D 139/50
[52] U.S. Cl. ................................. 424/200; 260/293.7; 260/326.82; 260/326.85; 544/123; 544/243; 544/320
[58] Field of Search ................ 260/256.5 R, 256.4 E; 544/123; 424/200

[56] References Cited

U.S. PATENT DOCUMENTS 3,966,730  6/1976  Hofer et al. ..................... 260/251 P

*Primary Examiner*—Donald G. Daus
*Assistant Examiner*—Lisa Jones
*Attorney, Agent, or Firm*—Burgess, Dinklage & Sprung

[57] ABSTRACT

O,O'-Dialkyl-O,O'-[2-aminopyrimidin(4,6)diyl]-bis-[(thiono)(thiol)phosphoric(phosphonic) acid esters] of the formula

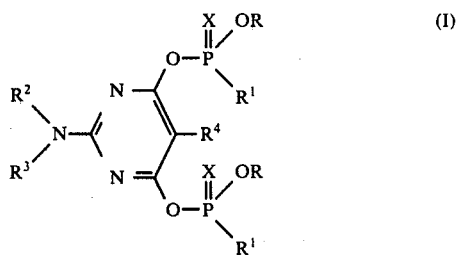

in which
R is alkyl,
$R^1$ is alkyl, alkoxy or alkylthio,
$R^2$ and $R^3$ each independently is alkyl or conjointly with the nitrogen atom form a heterocyclic ring which is optionally interrupted by at least one hetero-atom,
$R^4$ is hydrogen, alkyl or halogen, and
X is oxygen or sulphur,
which possess arthropodicidal properties.

10 Claims, No Drawings

O,O'-DIALKYL-O,O'-[2-AMINOPYRIMIDIN(4,6-)DIYL]-BIS-[(THIONO)(THIOL)PHOSPHORIC(-PHOSPHONIC) ACID ESTERS]

The present invention relates to and has for its objects the provision of particular new O,O'-dialkyl-O,O'-[2-aminopyrimidin(4,6)diyl]-bis-[(thiono)(thiol)phosphoric(phosphonic) acid esters] which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known from German Published Specifications DAS Nos. 1,170,401 and 1,197,878 and laid-open Netherlands Patent Application No. 6,713,142 that bis-[(thiono)phosphoric acid ester]diphenylsulphides and -disulphides, for example O,O,O',O'-tetramethyl- (Compound A) or -tetraethyl-O,O'-thiodi-p-phenylene-thionophosphoric acid ester (Compound B) and O,O-,O',O'-tetraethyl-O,O'-dithio-di-p-phenylene-thionophosphoric acid ester (Compound C), and pyrimidinylthionophosphoric acid esters, for example O,O-dimethyl-O-[2-diethylamino-6-methyl-pyrimidin(4)yl]-thionophosphoric acid ester (Compound D), possess insecticidal and acaricidal properties.

The present invention now provides, as new compounds, the substituted pyrimidine-bis-[(thiono)(thiol)-phosphoric(phosphonic) acid esters] of the general formula

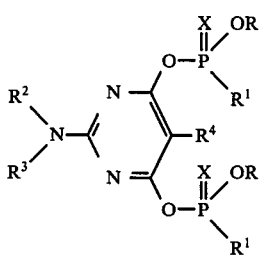 (I)

in which
R is alkyl,
$R^1$ is alkyl, alkoxy or alkylthio,
$R^2$ and $R^3$ each independently is alkyl or conjointly with the nitrogen atom form a heterocyclic ring which is optionally interrupted by at least one hetero-atom,
$R^4$ is hydrogen, alkyl or halogen, and
X is oxygen or sulphur.

Preferably, R represents straight-chain or branched alkyl with 1 to 5 carbon atoms, $R^1$ represents straight-chain or branched alkyl, alkoxy or alkylthio with, in each case, 1 to 4 carbon atoms, $R^2$ and $R^3$ each represent straight-chain or branched alkyl with 1 to 3 carbon atoms or conjointly represent an alkylene group with 3 to 5 carbon atoms, which can be interrupted by an oxygen atom, $R^4$ represents hydrogen, chlorine, bromine or straight-chain or branched alkyl with 1 to 3 carbon atoms and X represents sulphur.

Surprisingly, the substituted pyrimidine-bis[(thiono)(thiol)-phosphoric(phosphonic) acid esters] according to the invention exhibit a better insecticidal and acaricidal action than the corresponding, previously known compounds of similar structure and of the same type of action. The products according to the present invention thus represent a genuine enrichment of the art.

The invention also provides a process for the preparation of a substituted pyrimidine-bis[(thiono)(thiol)-phosphoric (phosphonic) acid ester] of the formula (I), in which a (thiono)(thiol) phosphoric(phosphonic) acid ester halide of the general formula

 (II)

in which
R, $R^1$ and X have the above-mentioned meanings and
Hal represents halogen, preferably chlorine, is reacted, if appropriate in the presence of a solvent or diluent, with a 4,6-dihydroxypyrimidine derivative of the general formula

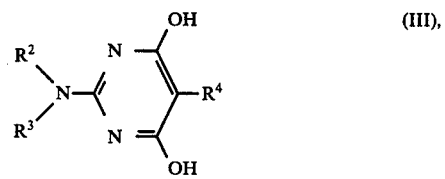 (III), in which
$R^2$, $R^3$ and $R^4$ have the above-mentioned meanings, the latter being employed either in the form of a di-alkali metal, di-alkaline earth metal or di-ammonium salt or as such in the presence of an acid acceptor.

If, for example, O,O-diethyl-thionophosphoric acid diester chloride and 5-chloro-2-diethylamino-4,6-dihydroxypyrimidine are used as starting materials, the course of the reaction can be represented by the following equation:

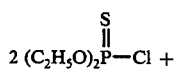

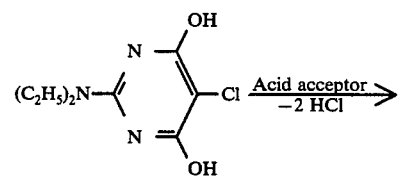

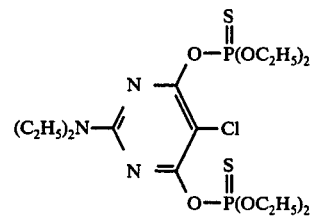

The (thiono)(thiol)phosphoric(phosphonic) acid ester halides (II) to be used as starting materials are known from the literature and can be prepared in accordance with generally customary processes. The following may be mentioned as individual examples thereof: O,O-dimethyl-, O,O-diethyl, O,O-di-n-propyl, O,O-di-iso-butyl, O,O-di-n-butyl-, O,O-di-iso-butyl, O,O-di-sec.-butyl-, O-methyl-O-ethyl-, O-methyl-O-n-propyl, O-methyl-O-iso-propyl, O-methyl-O-n-butyl-, O-methyl- O-iso-butyl-, O-methyl-O-sec.-butyl-, O-methyl-O-tert.-butyl-, O-ethyl-O-n-propyl-, O-ethyl-O-iso-propyl, O-ethyl-O-n-butyl, O-ethyl-O-sec.-butyl-, O-ethyl-O-iso-butyl-, O-n-propyl-O-butyl-, O-n-propyl-O-pentyl- and O-iso-propyl-O-butyl-phosphoric acid diester chloride and the corresponding thiono analogues; O,S-dimethyl-, O,S-diethyl-, O,S-di-n-propyl, O,S-di-iso-propyl-, O,S-di-n-butyl-, O,S-di-iso-butyl-, O,S-di-tert.-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl-, O-n-pentyl-S-ethyl-, O-n-pentyl-S-n-propyl-, O-n-pentyl-S-iso-propyl- and O-sec.-butyl-S-ethyl-thiolphosphoric acid diester halides and the corresponding thiono analogues; and O-methyl-, O-ethyl-, O-n-propyl-, O-iso-propyl-, O-n-butyl-, O-iso-butyl-, O-sec.-butyl-, O-tert.-butyl- and O-n-pentyl-methane-, -ethane-, -n-propane-, iso-propane-, -n-butane-, -iso-butane-, -tert.-butane- and -sec.-butane-phosphoric acid ester halides and the corresponding thiono analogues.

4,6-Dihydroxypyrimidine derivatives (III) are known from German Published Specification DOS No. 2,413,597 and can be prepared in accordance with generally customary processes, for example by reacting a guanidine derivative with malonic acid esters in the presence of bases, such as alkali metal alcoholates, in accordance with the following equation:

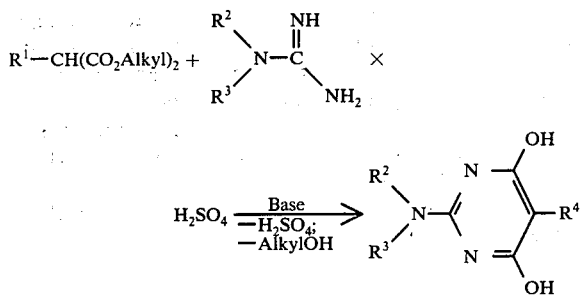

The following may be mentioned as individual examples of the 4,6-dihydroxypyrimidine derivatives (III): 2-dimethylamino-, 2-diethylamino,2-di-n-propylamino-, 2-di-isopropylamino-, 2-pyrrolidino-, 2-piperidino-, 2-morpholino-4,6-dihydroxy-pyrimidine, 2-dimethylamino-5-chloro-, 2-dimethylamino-5-bromo-, 2-dimethylamino-5-methyl-, 2-dimethylamino-5-ethyl-, 2-dimethylamino-5-n-propyl-, 2-dimethylamino-5-iso-propyl-, 2-diethylamino-5-chloro-, 2-diethylamino-5-bromo-, 2-diethylamino-5-methyl-, 2-diethylamino-5-ethyl-, 2-diethylamino-5-n-propyl-, 2-diethylamino-5-iso-propyl-, 2-di-n-propylamino-5-chloro-, 2-di-n-propylamino-5-bromo-, 2-di-n-propylamino-5-methyl-, 2-di-n-propylamino-5-ethyl-, 2-di-n-propylamino-5-n-propyl-, 2-di-n-propylamino-5-iso-propyl-, 2-di-iso-propylamino-5-chloro-, 2-di-iso-propylamino-5-bromo-, 2-di-iso-propylamino-5-methyl-, 2-di-iso-propylamino-5-ethyl-, 2-di-iso-propylamino-5-n-propyl-, 2-di-iso-propylamino-5-iso-propyl-, 2-pyrrolidino-5-chloro-, 2-pyrrolidino-5-bromo-, 2-pyrrolidino-5-methyl-, 2-pyrrolidino-5-ethyl-, 2-pyrrolidino-5-n-propyl-, 2-pyrrolidino-5-iso-propyl-, 2-piperidino-5-chloro-, 2-piperidino-5-bromo-, 2-piperidino-5-methyl-, 2-piperidino-5-ethyl-, 2-piperidino-5-n-propyl-, 2-piperidino-5-iso-propyl-, 2-morpholino-5-chloro-, 2-morpholino-5-bromo-, 2-morpholino-5-methyl-, 2-morpholino-5-ethyl-, 2-morpholino-5-n-propyl- and 2-morpholino-5-iso-propyl-4,6-dihydroxypyrimidine.

The process for the preparation of the compounds according to the invention is preferably carried out in the presence of a suitable solvent or diluent. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 20° and 120° C, preferably at from 40° to 60° C.

In general, the reaction is allowed to take place under normal pressure.

To carry out the process, preferably two moles of (thiono)(thiol)phosphoric(phosphonic) acid ester halide (II) are employed per mole of 4,6-dihydroxypyrimidine derivative (III). Preferably, the 4,6-dihydroxypyrimidine derivative (III), in one of the stated solvents and, if appropriate, in the presence of an acid acceptor, is taken, and the phosphorus component is added dropwise. After stirring for one or more hours, in most cases at an elevated temperature, the reaction mixture is poured into an organic solvent, for example toluene, and worked up in the usual manner, for example by separating off the organic phase, washing and drying the latter and distilling off the solvent.

The new compounds are in most cases obtained in the form of oils some of which cannot be distilled without decomposition, but are freed of the last volatile constituents by so-called "slight distillation", that is to say by prolonged heating under reduced pressure to moderately elevated temperatures, and are purified in this way. They are characterized by the refractive index. Some compounds are obtained in a crystalline form and are characterized by their melting point.

As already mentioned, the substituted pyrimidine-bis[(thiono)(thiol)phosphoric(phosphonic) acid esters] according to the invention are distinguished by an excellent insecticidal and acaricidal activity. They are active against plant pests, pests harmful to health and pests of stored products. They possess a low phytotoxicity and a good action against sucking and biting insects and against mites.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating arthropod pests, especially insects and arachnids which are encountered in agriculture, in forestry, in the protection of stored products and of materials, and in the hygiene field.

They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blanlulus guttulatus;* from the class of the Chilopoda, for example *Geophilus carpophagus* and Scutigera spec.; from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentials* and *Schistocerca gregaria;* from the order of the Dermaptera, for example *Forficula auricularia;* from the order of the Isoptera, for example Reticulitermes spp.; from the order of the Anoplura, for example *Phylloxera vastatrix,* Pemphigus spp., *Pediculus humanus corporis,* Haematopinus spp. and Linognathus spp.; from the order to the Mallophaga, for example Trichodectes spp., and Damalinea spp.; from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Neophotettix cincticeps, Lecanium corni, Saissetia oleae, Laodelphax striatellus, Nilaparvata lugens, Aonidiella aurantii, Aspidiotus hederea,* Pseudococcus spp. and Psylla spp.; from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella, Pieris* spp., Chilo spp., *Pyrausta nubilalis, Ephestia kühniella, Gallerai mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Cryzaephilus surinamensis,* Anthonomus spp., Sitophilus spp., *Ctiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of Hymenoptera, for example Diprion spp., Hoplocampa spp., Lasius spp., *Monomorium pharaonis* and *Vespa spp.; from the order of the Diptera, for example Aedes spp., Anopheles spp., Culex spp., Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp. Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.; from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panoychus spp., and Tetranychus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. diichlorodifluoromethane or trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed whereas 0% meant that none of the aphids were killed.

The active compounds, the concentrations of the active compounds, the evaluation times and the results can be seen from Table 1:

Table 1

(Myzus test)

| Active compound | | Active compound concentration in % | Degree of destruction in % after 1 day |
|---|---|---|---|
| (CH₃O)₂P(=S)−O−C₆H₄−S−C₆H₄−O−P(=S)(OCH₃)₂ (known) | (A) | 0.1<br>0.01 | 100<br>0 |
| (C₂H₅O)₂P(=S)−O−C₆H₄−S−C₆H₄−O−P(=S)(OC₂H₅)₂ (known) | (B) | 0.1<br>0.01 | 100<br>0 |
| (C₂H₅O)₂P(=S)−O−C₆H₄−S−S−C₆H₄−O−P(=S)(OC₂H₅)₂ (known) | (C) | 0.1 | 0 |
| 2-(CH₃)₂N-pyrimidine-4,6-diyl bis[O,O-dimethyl phosphorothioate] | (3) | 0.1<br>0.01 | 100<br>100 |
| 2-(CH₃)₂N-pyrimidine-4,6-diyl bis[O,O-diethyl phosphorothioate] | (1) | 0.1<br>0.01 | 100<br>100 |
| 2-(CH₃)₂N-5-Cl-pyrimidine-4,6-diyl bis[O,O-diethyl phosphorothioate] | (12) | 0.1<br>0.01 | 100<br>100 |
| 2-(CH₃)₂N-pyrimidine-4,6-diyl bis[O-methyl ethylphosphonothioate] | (5) | 0.1<br>0.01 | 100<br>100 |

Table 1-continued
(*Myzus* test)

| Active compound | Active compound concentration in % | Degree of destruction in % after 1 day |
|---|---|---|
| (CH₃)₂N-[pyrimidine with two O-P(=S)(OC₂H₅)(CH₃) groups] (4) | 0.1<br>0.01 | 100<br>100 |
| (CH₃)₂N-[pyrimidine with two O-P(=S)(OC₂H₅)(C₂H₅) groups] (6) | 0.1<br>0.01 | 100<br>100 |
| (CH₃)₂N-[pyrimidine with two O-P(=S)(OCH(CH₃)₂)(CH₃) groups] (2) | 0.1<br>0.01 | 100<br>99 |
| (C₂H₅)₂N-[pyrimidine with two O-P(=S)(OCH₃)₂ groups] (8) | 0.1<br>0.01 | 100<br>95 |
| (C₂H₅)₂N-[pyrimidine with two O-P(=S)(OC₂H₅)(C₂H₅) groups] (9) | 0.1<br>0.01 | 100<br>90 |
| (C₂H₅)₂N-[pyrimidine with two O-P(=S)(OC₂H₅)₂ groups] (7) | 0.1<br>0.01 | 100<br>90 |

Table 1-continued
(*Myzus* test)

| Active compound | Active compound concentration in % | Degree of destruction in % after 1 day |
|---|---|---|
| (18) Piperidine-N-pyrimidine with O-P(=S)(OC₂H₅)(C₂H₅) groups at 4,6-positions | 0.1<br>0.01 | 100<br>100 |
| (19) Piperidine-N-pyrimidine with O-P(=S)(OC₂H₅)₂ groups at 4,6-positions | 0.1<br>0.01 | 100<br>100 |
| (16) Piperidine-N-pyrimidine with O-P(=S)(OC₂H₅)(C₂H₅) groups at 4,6-positions | 0.1<br>0.01 | 100<br>95 |
| (14) Piperidine-N-pyrimidine with O-P(=S)(OC₂H₅)₂ groups at 4,6-positions | 0.1<br>0.01 | 100<br>99 |
| (22) Morpholine-N-pyrimidine with O-P(=S)(OCH₃)₂ groups at 4,6-positions | 0.1<br>0.01 | 100<br>98 |
| (20) Morpholine-N-pyrimidine with O-P(=S)(OC₂H₅)₂ groups at 4,6-positions | 0.1<br>0.01 | 100<br>100 |

Table 1-continued
(Myzus test)

| Active compound | Active compound concentration in % | Degree of destructio in % after 1 day |
|---|---|---|
| (structure 23): (CH$_3$)$_2$N-pyrimidine with O-P(S)(OC$_2$H$_5$)$_2$ groups at both positions | 0.1<br>0.01 | 100<br>100 |

(23)

EXAMPLE 2

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from Table 2:

Table 2
(Tetranychus test)

| Active compound | Active compound concentration in % | Degree of destruction in % after 2 days |
|---|---|---|
| (C$_2$H$_5$O)$_2$P(S)-O-C$_6$H$_4$-S-S-C$_6$H$_4$-O-P(S)(OC$_2$H$_5$)$_2$ (known) (c) | 0.1 | 0 |
| (CH$_3$)$_2$N-pyrimidine with O-P(S)(OC$_2$H$_5$)(CH$_3$) groups (4) | 0.1 | 98 |
| (CH$_3$)$_2$N-pyrimidine with O-P(S)(OCH(CH$_3$)$_2$)(CH$_3$) groups (2) | 0.1 | 99 |
| pyrrolidinyl-pyrimidine with O-P(S)(OC$_2$H$_5$)$_2$ groups (19) | 0.1 | 90 |

EXAMPLE 3

LT$_{100}$ test for *Diptera*

Test insects: *Musca domestica*
Solvent: Acetone 2 parts by weight of active compound were taken up in 1,000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was continuously observed. The time which was necessary for 100% destruction was determined.

The test insects, the active compounds, the concentrations of the active compounds and the times at which there was 100% destruction can be seen from Table 3:

EXAMPLE 4

LD$_{100}$ test

Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denoted that all test insects had been killed; 0% denoted that no test insects had been killed.

The active compounds, the concentrations of the

Table 3

(LT$_{100}$ test for *Diptera/Musca domestica*)

| Active compound | Active compound concentration of the solution in % | LT$_{100}$ in minutes |
|---|---|---|
| 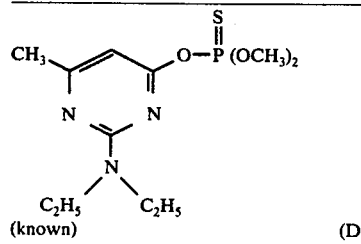 (known) (D) | 0.02 | 135 |
| 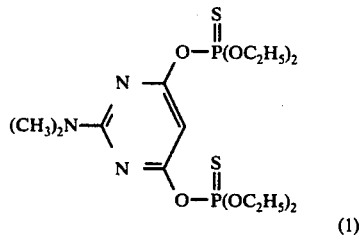 (1) | 0.02 | 80 |
| 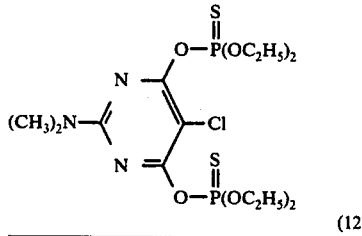 (12) | 0.02 | 85 | active compounds, the test insects and the results can be seen from Table 4:

Table 4

(LD$_{100}$ test/*Sitophilus granarius*)

| Active compound | Active compound concentration of the solution in % | Degree of destruction in % |
|---|---|---|
| 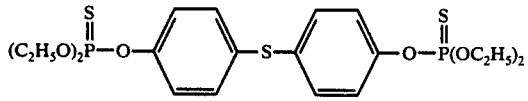 | 0.2 | 100 |
| | 0.02 | 0 |

Table 4-continued (LD$_{100}$ test/*Sitophilus granarius*)

| Active compound (known) | Active compound concentration of the solution in % | Degree of destruction in % |
|---|---|---|
| (B) structure: (CH$_3$)$_2$N-pyrimidine with O-P(=S)(OC$_2$H$_5$)$_2$ groups | 0.02 | 100 |
| (1) structure: (CH$_3$)$_2$N-pyrimidine with O-P(=S)(OCH$_3$)$_2$ groups | 0.02 | 100 |
| (3) structure: (CH$_3$)$_2$N-pyrimidine with O-P(=S)(OC$_2$H$_5$)(CH$_3$) groups | 0.02 | 100 |
| (4) structure: (C$_2$H$_5$)$_2$N-pyrimidine with O-P(=S)(OC$_2$H$_5$)$_2$ groups | 0.02 | 100 |
| (7) structure: (C$_2$H$_5$)$_2$N-pyrimidine with O-P(=S)(OCH$_3$)$_2$ groups | 0.02 | 100 |
| (8) structure: piperidinyl-pyrimidine with O-P(=S)(OC$_2$H$_5$)$_2$ groups | 0.02 | 100 |
| (14) | | |

Table 4-continued

| | (LD$_{100}$ test/*Sitophilus granarius*) | |
|---|---|---|
| Active compound | Active compound concentration of the solution in % | Degree of destruction in % |
| 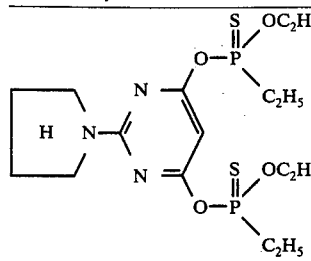 (18) | 0.02 | 100 |
| 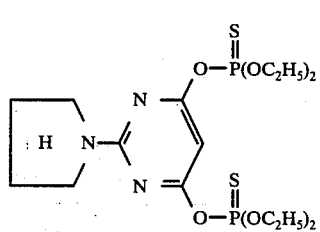 (19) | 0.02 | 100 |
| 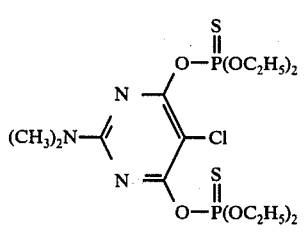 (12) | 0.02 | 100 |

The process of the present invention is illustrated by the following preparative examples.

EXAMPLE 5

(a) 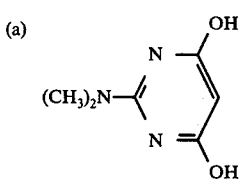

136 g (0.5 mol) of N,N-dimethylguanidine sulphate were added to a solution of 162 g (3 mol) of sodium methylate in 1 l of methanol at 0° to 5° C. 160 g (1 mol) of malonic acid diethyl ester were then allowed to run in without cooling and the mixture was stirred for 24 hours at room temperature. The solvent was then distilled off in vacuo and the residue was dissolved in water. The solution was brought to approximately pH 5 by adding glacial acetic acid; it was then cooled to 0°–5° C and the product which had precipitated was filtered off. 75 g (48% of theory) of 2-dimethylamino-4,6-dihydroxypyrimidine were thus obtained in the form of a colorless powder of melting point > 300° C.

The following compounds of the formula

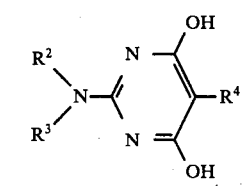 (III), could be prepared analogously:

Table 5

| R$^2$ | R$^3$ | R$^4$ | Yield (% of theory) | Melting point (° C) |
|---|---|---|---|---|
| H$_5$C$_2$— | H$_5$C$_2$— | H | 60 | 233 (decomp) |
| H$_3$C— | H$_3$C— | —CH$_3$ | 41 | >270 |
| H$_3$C— | H$_3$C— | —Cl | 51 | >250 |
| —(CH$_2$)$_5$— | | H | 66 | 236 (decomp) |
| —(CH$_2$)$_4$— | | H | 85 | >300 |
| —CH$_2$CH$_2$OCH$_2$CH$_2$— | | H | 69 | >300 |
| H$_5$C$_2$— | H$_5$C$_2$— | Cl | 56 | >300 |

(b) 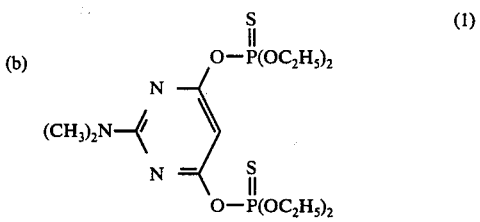 (1)

A mixture of 15.5 g (0.1 mol) of 2-dimethylamino-4,6-dihydroxypyrimidine, 34.5 g (0.25 mol) of potassium carbonate, 200 ml of acetonitrile and 37.7 g (0.2 mol) of O,O-diethyl-thionophosphoric acid diester chloride was stirred for 15 hours at 45° to 50° C. 400 ml of toluene were then added to the reaction mixture, which was washed twice with 300 ml of water at a time. The organic phase was dried over sodium sulphate, the solvent was then removed under reduced pressure and the residue was subjected to slight distillation. 35 g (76% of theory) of O,O,O',O'-tetraethyl-O,O'-[2-dimethylaminopyrimidin(4,6)-diyl]-bis-thionophosphoric acid ester were obtained in the form of a brown oil having a refractive index $n_D^{25}$ of 1.5206.

The following compounds of the formula

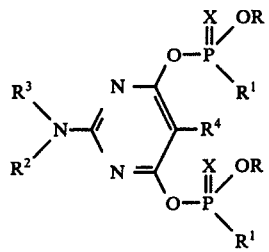

could be prepared analogously:

1. An O,O'-dialkyl-O,O'-2-aminopyrimidin(4,6)-diyl-bis-(thiono/(thiol) phosphoric (phosphonic acid) ester of the formula

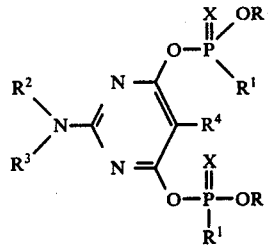

in which
R is alkyl with 1 to 5 carbon atoms,
$R_1$ is alkyl, alkoxy, or alkyl thio with 1 to 4 carbon atoms, $R^2$ and $R^3$ each independently is alkyl with 1 to 3 carbon atoms or conjointly are an alkylene group with 3 to 5 carbon atoms which can be interrupted by an oxygen atom, $R^4$ is hydrogen, alkyl with 1 to 3 carbon atoms or halogen, and X is oxygen or sulphur.

2. A compound according to claim 1, in which $R^4$ is

Table 6

| Compound No. | R | $R^1$ | $R^2$ | $R^3$ | $R^4$ | X | Yield (% of theory) | Physical data (refractive index melting point °C) |
|---|---|---|---|---|---|---|---|---|
| 2 | iso-$C_3H_7$— | $H_3C$— | —$CH_3$ | —$CH_3$ | H | S | 60 | $n_D^{25}$:1.5362 |
| 3 | $H_3C$— | $H_3CO$— | —$CH_3$ | —$CH_3$ | H | S | 38 | $n_D^{20}$:1.5465 |
| 4 | $H_5C_2$— | $H_3C$— | —$CH_3$ | —$CH_3$ | H | S | 59 | $n_D^{20}$:1.5485 |
| 5 | $H_3C$— | $H_5C_2$— | —$CH_3$ | —$CH_3$ | H | S | 76 | $n_D^{21}$:1.5568 |
| 6 | $H_5C_2$— | $H_5C_2$— | —$CH_3$ | —$CH_3$ | H | S | 80 | $n_D^{15}$:1.5439 |
| 7 | $H_5C_2$— | $H_5C_2O$— | —$C_2H_5$ | —$C_2H_5$ | H | S | 87 | $n_D^{22}$:1.5177 |
| 8 | $H_3C$— | $H_3CO$— | —$C_2H_5$ | —$C_2H_5$ | H | S | 49 | $n_D^{22}$:1.5408 |
| 9 | $H_5C_2$— | $H_5C_2$— | —$C_2H_5$ | —$C_2H_5$ | H | S | 88 | $n_D^{22}$:1.5378 |
| 10 | $H_5C_2$— | $H_5C_2O$— | —$CH_3$ | —$CH_3$ | —$CH_3$ | S | 70 | 62 |
| 11 | $H_5C_2$— | $H_5C_2$— | —$CH_3$ | —$CH_3$ | —$CH_3$ | S | 78 | $n_D^{20}$:1.5439 |
| 12 | $H_5C_2$— | $H_5C_2O$— | —$CH_3$ | —$CH_3$ | Cl | S | 70 | $n_D^{23}$:1.5010 |
| 13 | $H_5C_2$— | n-$H_3C_7S$— | —$CH_3$ | —$CH_3$ | Cl | S | 65 | $n_D^{23}$:1.5621 |
| 14 | $H_5C_2$— | $H_5C_2O$— | —$(CH_2)_5$— | | H | S | 74 | $n_D^{21}$:1.5310 |
| 15 | $H_3C$— | $H_3CO$— | —$(CH_2)_5$— | | H | S | 57 | $n_D^{21}$:1.5550 |
| 16 | $H_5C_2$— | $H_5C_2$— | —$(CH_2)_5$— | | H | S | 84 | $n_D^{21}$:1.5503 |
| 17 | $H_3C$— | $H_3CO$— | —$(CH_2)_4$— | | H | S | 25 | $n_D^{22}$:1.5540 |
| 18 | $H_5C_2$— | $H_5C_2$— | —$(CH_2)_4$— | | H | S | 63 | $n_D^{22}$:1.5330 |
| 19 | $H_5C_2$— | $H_5C_2O$— | —$(CH_2)_4$— | | H | S | 37 | $n_D^{22}$:1.5149 |
| 20 | $H_5C_2$— | $H_5C_2O$— | —$CH_2$—$CH_2$—O—$CH_2$—$CH_2$— | | H | S | 80 | 52 |
| 21 | $H_5C_2$— | $H_5C_2$— | —$CH_2$—$CH_2$—O—$CH_2$—$CH_2$— | | H | S | 51 | 93 |
| 22 | $H_3C$— | $H_3CO$— | —$CH_2$—$CH_2$—O—$CH_2$—$CH_2$— | | H | S | 53 | $n_D^{23}$:1.5537 |
| 23 | $H_5C_2$— | $H_5C_2O$— | —$CH_3$ | —$CH_3$ | H | O | 63 | $n_D^{20}$:1.4813 |
| 24 | $H_5C_2$— | $H_5C_2$— | —$C_2H_5$ | —$C_2H_5$ | Cl | S | 53 | $n_D^{25}$:1.4590 |
| 25 | $H_5C_2$— | $H_5C_2O$— | —$C_2H_5$ | —$C_2H_5$ | Cl | O | 58 | $n_D^{25}$:1.4912 |
| 26 | $H_5C_2$— | n-$H_3C_7S$— | —$C_2H_5$ | —$C_2H_5$ | Cl | S | 61 | $n_D^{25}$:1.5515 |
| 27 | $H_5C_2$— | $H_5C_2O$— | —$C_2H_5$ | —$C_2H_5$ | Cl | S | 43 | $n_D^{25}$:1.5228 |

Other compounds which can be similarly prepared include:

Table 7

| R | $R^1$ | $R^2$ | $R^3$ | $R^4$ | X |
|---|---|---|---|---|---|
| n-$C_5H_{11}$— | n-$C_4H_9O$— | $CH_3$ | $C_2H_5$ | H | S |
| sec.—$C_4H_9$— | sec.—$C_4H_9$— | $CH_3$ | $CH_3$ | H | S |
| $CH_3$ | $CH_3S$— | n-$C_3H_7$ | n-$C_3H_7$ | Br | S |

It will be appreciated that the instant specification and examples are set forth by way of illustration and not limitation, and that various modifications and changes may be made without departing from the spirit and scope of the present invention.

What is claimed is:

hydrogen, chlorine, bromine or alkyl with 1 to 3 carbon atoms, and X is sulphur.

3. The compound according to claim 1 wherein such compound is O,O,O',O'-tetramethyl-O,O'-[2-dimethylaminopyrimidin(4,6)diyl]-bis-thionophosphoric acid ester of the formula 4. The compound according to claim 1 wherein such compound is O,O'-diethyl-O,O'-[2-dimethylaminopyrimidin(4,6)diyl]-bis-methanethionophosphonic acid ester of the formula

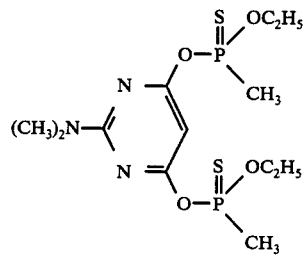

5. The compound according to claim 1 wherein such compound is O,O'-dimethyl-O,O'-[2-dimethylaminopyrimidin(4,6)diyl]-bis-ethanethionophosphonic acid ester of the formula

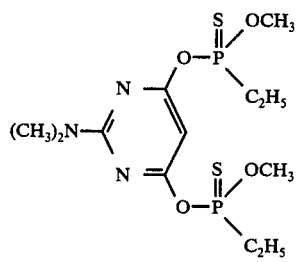

6. The compound according to claim 1 wherein such compound is O,O,O',O'-tetraethyl-O,O'-[2-dimethylaminopyrimidin(4,6)diyl]-bis-thionophosphoric acid ester of the formula

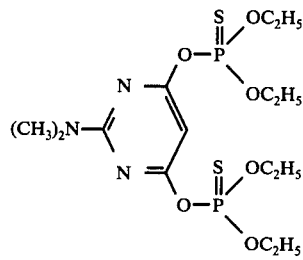

7. The compound according to claim 1 wherein such compound is O,O,O',O'-tetraethyl-O,O'-[2-dimethylamino-5-chlor-pyrimidin(4,6)-diyl]-bis-thionophosphoric acid ester of the formula

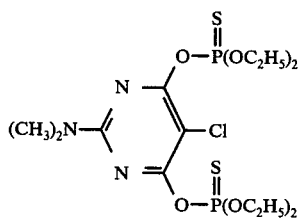

8. An insecticidal/acaricidal composition containing as active ingredient an insecticidally/acaricidally effective amount of a compound according to claim 1 in admixture with a diluent.

9. A method of combating insects and acarids which comprises applying to the insects and acarids, or to a habitat thereof, an arthropodicidally effective amount of a compound according to claim 1.

10. The method according to claim 9 in which said compound is
O,O,O',O'-tetramethyl-O,O'-[2-dimethylaminopyrimidin(4,6)diyl]-bis-thionophosphoric acid ester,
O,O'-diethyl-O,O'-[2-dimethylaminopyrimidin(4,6)diyl]-bis-methanethionophosphonic acid ester,
O,O'-dimethyl-O,O'-[2-dimethylaminopyrimidin(4,6)diyl]-bis-ethanethionophosphonic acid ester,
O,O,O',O'-tetraethyl-O,O'-[2-dimethylamino-5-chlor-pyrimidin(4,6)diyl]-bis-thionophosphoric acid ester, or
O,O,O',O',tetraethyl-O,O'-2[2-dimethylamino-5-chlor-pyrimidin(4,6)diyl]-bis-thionophosphoric acid ester.

* * * * *